United States Patent [19]

Krass

[11] 4,375,981

[45] Mar. 8, 1983

[54] METHOD FOR CONTROLLING WEED GROWTH USING HERBICIDALLY 5-(2-CHLORO-4-TRIFLUOROMETHYL)-, OR (4-TRIFLUOROMETHYL OR 2,6-DICHLORO-4-TRIFLUOROMETHYL-PHENOXY)-2-NITRO-SUBSTITUTED CARBONYL OXIME-O-ALKYL ETHERS

[75] Inventor: Dennis K. Krass, Canal Fulton, Ohio

[73] Assignee: PPG Industries, Inc., Pittsburgh, Pa.

[21] Appl. No.: 208,966

[22] Filed: Nov. 21, 1980

Related U.S. Application Data

[62] Division of Ser. No. 38,746, May 14, 1979, Pat. No. 4,263,227.

[51] Int. Cl.$^3$ ............................ A01N 35/10; C07C 131/00
[52] U.S. Cl. ............................................ 71/121; 564/256
[58] Field of Search ............................................ 71/121

[56] References Cited

U.S. PATENT DOCUMENTS

| | | | |
|---|---|---|---|
| 3,652,645 | 3/1972 | Theissen | 260/471 R |
| 3,776,715 | 12/1973 | Theissen | 71/111 |
| 3,798,276 | 3/1974 | Bayer et al. | 260/612 R |
| 3,845,126 | 10/1974 | Giraudon et al. | 564/256 |
| 3,907,866 | 9/1975 | Theissen | 71/111 |
| 3,914,300 | 10/1975 | Haddock et al. | 564/256 |
| 3,928,416 | 12/1975 | Bayer | 71/111 |
| 3,976,470 | 8/1976 | Bayer | 71/100 |
| 3,979,437 | 9/1976 | Theissen | 71/111 |
| 3,983,168 | 9/1976 | Theissen | 71/111 |
| 3,989,737 | 11/1976 | Swaki et al. | 564/256 |
| 4,039,588 | 8/1977 | Wilson et al. | 260/465 G |
| 4,059,435 | 11/1977 | Johnson | 71/105 |
| 4,063,929 | 12/1977 | Bayer et al. | 71/115 |
| 4,079,149 | 3/1978 | Henry | 564/256 |
| 4,093,446 | 6/1978 | Bayer et al. | 71/109 |
| 4,277,624 | 7/1981 | Yoshimoto et al. | 71/121 |

FOREIGN PATENT DOCUMENTS

| | | |
|---|---|---|
| 49-60635 | 12/1975 | Japan. |
| 52-46286 | 11/1977 | Japan ............................... 71/121 |
| 1096037 | 12/1967 | United Kingdom ............... 564/256 |

OTHER PUBLICATIONS

Yoshimoto, et al., "Chemical Abstracts", vol. 84 (1975), col. 13515f.

Primary Examiner—Donald G. Daus
Assistant Examiner—James H. Turnipseed
Attorney, Agent, or Firm—Edward J. Whitfield; Robert J. Grassi

[57] ABSTRACT

Disclosed are compounds such as 5-(2-chloro-4-trifluoromethylphenoxy)-2-nitroacetophenone oxime-O-methyl ether, and the method of controlling weeds, such as wild oats with the compounds.

5 Claims, No Drawings

METHOD FOR CONTROLLING WEED GROWTH USING HERBICIDALLY 5-(2-CHLORO-4-TRIFLUOROMETHYL)-, OR (4-TRIFLUOROMETHYL OR 2,6-DICHLORO-4-TRIFLUOROMETHYL-PHENOXY)-2-NITRO-SUBSTITUTED CARBONYL OXIME-O-ALKYL ETHERS

This is a division of application Ser. No. 38,746, filed May 14, 1979, now U.S. Pat. No. 4,263,227.

BACKGROUND OF THE INVENTION

1. Field of the Invention

The invention pertains to 5-(4-trifluoromethyl, or (2-chloro-4-trifluoromethyl) or (2,6-dichloro-4-trifluoromethylphenoxy-2-nitro substituted carbonyl oxime-O-alkyl ethers, such as 5-(2-chloro-4-trifluoromethylphenoxy)-2-nitro-acetaphenone oxime-O-methyl ether and their use to control weeds, i.e., wild oats.

2. Description of the Prior Art

The prior art describes diphenyl ethers in general. The prior art, however, is silent concerning the novel compounds of this invention and their use as preemergence herbicides against certain weeds and postemergence herbicides against weeds.

SUMMARY OF THE INVENTION

The invention concerns novel herbicidal compounds graphically represented by general Formula I

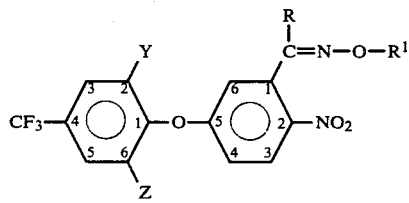

wherein: Y is chlorine or hydrogen; Z is chlorine when Y is chlorine, or Z is hydrogen when Y is chlorine or hydrogen; R is hydrogen or an alkyl of up to three carbon atoms, and $R^1$ is an alkyl of up to four carbon atoms; as well as the method of preparing these novel compounds and the control of weeds with the compounds; for example 5-(2-chloro-4-trifluorophenoxy)-2-nitroacetophenone oxime-O-methyl ether in its anti and syn isomer forms is useful for controlling the weeds described herein.

DESCRIPTION OF THE PREFERRED EMBODIMENTS

The novel agriculturally useful 5(2-chloro-4-trifluoromethyl- or 4-trifluoromethyl or 2,6-dichloro-4-trifluoromethylphenoxy)-2-nitrosubstituted carbonyl oxime alkyl ethers in both their anti and syn forms are graphically represented by general Formula I wherein:

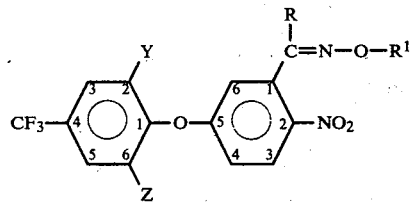

Y is chlorine or hydrogen;
Z is chlorine when Y is chlorine, or Z is hydrogen when Y is chlorine or hydrogen;
R is hydrogen or an alkyl of up to three carbon atoms, and
$R^1$ is an alkyl of up to four carbon atoms.

Representative compounds are those in which

I. R is an alkyl of up to three carbon atoms; such as
- 5-(4-trifluoromethylphenoxy)-2-nitrobutyrophenone oxime-O-t-butyl ether,
- 5-(2-chloro-4-trifluoromethylphenoxy)-2-nitro-2-methylpropiophenone oxime-O-sec butyl ether,
- 5-(2,6-dichloro-4-trifluoronethylphenoxy)-2-nitro butyrophenone oxime-O-isopropyl ether,
- 5-(4-trifluoromethylphenoxy)-2-nitropropiophenone oxime-O-propyl ether,
- 5-(2-chloro-4-trifluoromethylphenoxy)-2-nitropropiophenone oxime-O-methyl ether,
- 5-(2-chloro-4-trifluoromethylphenoxy)-2-nitroacetophenone oxime-O-ethyl ether,
- 5-(2-chloro-4-trifluoromethylphenoxy)-2-nitroacetophenone oxime-O-isobutyl ether,
- 5-(2,6-dichloro-4-trifluoromethylphenoxy)-2-nitroacetophenone oxime-O-propyl ether, II. R is hydrogen; such as:
- 5-(4-trifluoromethylphenoxy)-2-nitrobenzaldoxime-O-t-butyl ether,
- 5-(2-chloro-4-trifluoromethylphenoxy)-2-nitrobenzaldoxime-O-methyl ether,
- 5-(2,6-dichloro-4-trifluoromethylphenoxy)-2-nitrobenzaldoxime-O-ethyl ether,
- 5-(4-trifluoromethylphenoxy)-2-nitrobenzaldoxime-O-propyl ether.

As used herein and in the claims, the word "compound" and the name of compound, for example 5-(2-chloro-4-trifluorophenoxy)-2-nitroacetophenone oxime-O-methyl ether, refers to the two isomers of the compound, the syn and anti isomers.

Although all the compounds as disclosed herein are useful for the purposes disclosed herein, some compounds are preferred over others. Those compounds in which R is methyl are preferred to those compounds in which R is hydrogen or an alkyl of from two to three carbon atoms. Those compounds in which Y and Z are as mentioned herein, in order of increasing preference are; those in which Y and Z are hydrogen, those in which Y and Z are chlorine, and those in which Y is chlorine and Z is hydrogen. Those compounds in which $R^1$ is methyl or ethyl are greatly preferred.

The highly preferred compounds graphically represented by general Formula I are:
- 5-(2-chloro-4-trifluoromethylphenoxy)-2-nitrobenzaldoxime-O-methyl ether,
- 5-(2-chloro-4-trifluoromethylphenoxy)-2-nitro benzaldoxime-O-ethyl ether,
- 5-(2-chloro-4-trifluoromethylphenoxy)-2-nitroacetophenone oxime-O-ethyl ether, and 5-(2-chloro-4-trifluoromethylphenoxy)-2-nitroacetophenone oxime-O-methyl ether.

The most preferred compound is 5-(2-chloro-4-trifluoromethylphenoxy)-2-nitroacetophenone oxime-O-methyl ether.

SYNTHESIS a. General Procedure

The synthesis of the 5-(substituted-phenoxy)-2-nitro substituted carbonyl oxime ethers, described herein proceeds according to the reaction equations (1), (2), (3) and (4) shown below:

The appropriate trifluoromethyl halo substituted compound of Formula V where Y and Z are as described herein is reacted with a salt of a metal-3-substituted carboxyl phenoxide of Formula VI, where M is a cation of sodium, (Na+), potassium (K+) to form a compound of Formula VII, which is separated from the reaction mixture and nitrated to a compound of Formula II. Note the step of nitrating also includes the step of separating the compound of Formula VI from the nitrating reaction mixture.

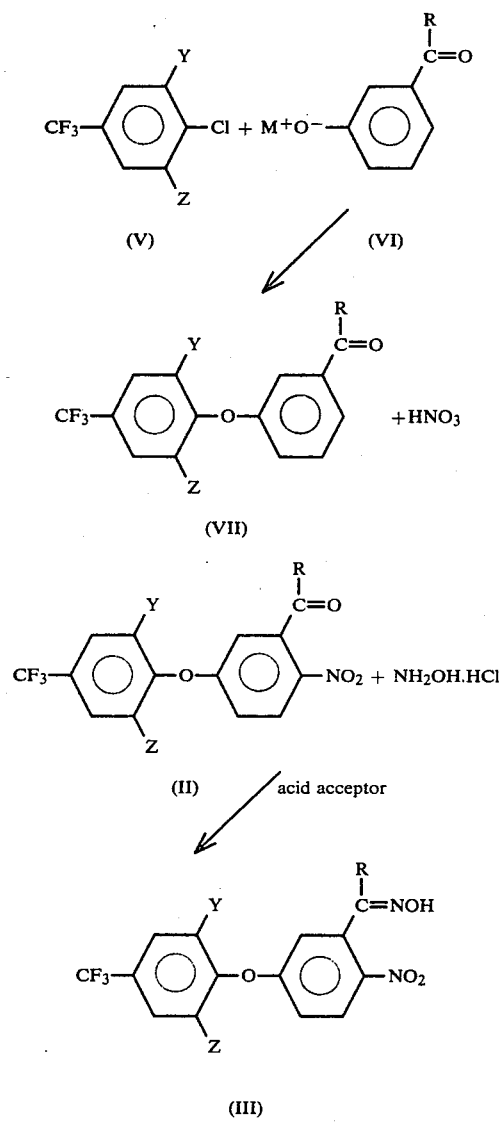

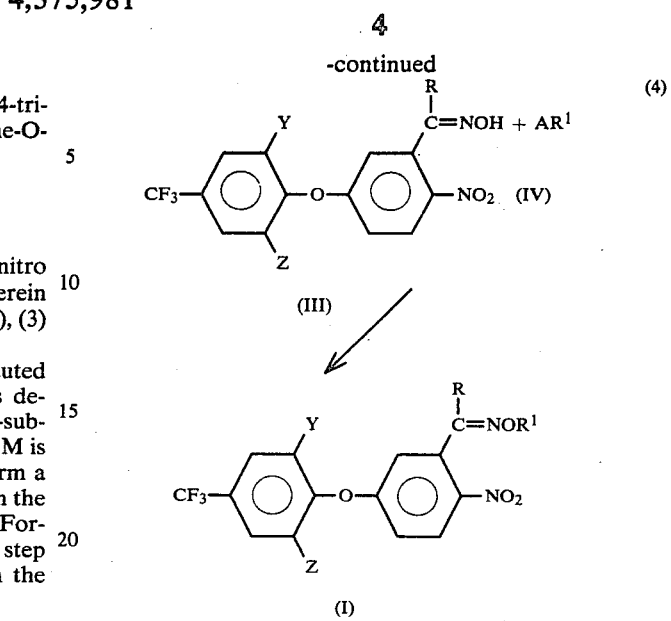

The appropriate carbonyl compound (aldehyde) graphically represented by general Formula II wherein Y and Z, are as defined herein and R is hydrogen; for example (0.001 mole) is dissolved in 20 milliliters of tetrahydrofuran (THF) and 12 milliliters of absolute ethanol. To this stirred solution is added hydroxylamine hydrochloride (0.012 mole) in 1 milliliter of water, and then 0.6 grams (0.015 mole) sodium hydroxide in 5 milliliters of water. The solution is stirred overnight at ambient temperature and the THF and ethanol is stripped off in vacuo, leaving a two-phase system. The oil phase is dissolved in chloroform ($HCCl_3$) and then separated from the aqueous phase. The chloroform layer is then extracted with water, and with a saturated sodium chloride solution, and then dried over anhydrous magnesium sulfate ($MgSO_4$). Filtration and evaporation affords the crude product of 5-(2-chloro-4-trifluoromethyl-, or 4-trifluoromethyl- or 2,6-dichloro-4-trifluoromethylphenoxy) -2-nitro substituted carbonyl oximes of general Formula III wherein Y, Z, and R are as defined herein. The crude product can be recrystallized in carbon tetrachloride ($CCl_4$).

An alternate procedure is used when R of Formula II is an alkyl described herein. This procedure employs anhydrous conditions. For example, (0.0056 mol) of the appropriate carbonyl compound of general Formula II, wherein Y and Z are as defined herein and R is an alkyl defined herein, is dissolved in 20 ml. of a 1:1 mixture of absolute ethanol and dry benzene. To this solution is added 0.77 grams of hydroxylamine hydrochloride in 15 ml. of absolute ethanol and (0.0112 mol) of a tertiary amine, such as triethylamine, which is preferred. The solution is heated to reflux and the water formed in the reaction is azeotroped off. After refluxing for 18 hours, solvent is removed in vacuo, the residue dissolved in chloroform and extracted with water and saturated sodium chloride solution and dried over anhydrous magnesium sulfate. Filtration and evaporation affords the crude product oximes of general Formula III.

The appropriate oxime of general Formula III, prepared as above, (0.004 mole) is dissolved in four milliliters of ethanol and added to a solution of 0.1 gram (0.0045 mole) of the appropriate halo-alkyl compound of general Formula IV wherein $R^1$ is as defined herein, and A is chlorine, bromine, or iodine, and the reaction is followed by thin layer chromatography. The solution can be heated at reflux, if the reaction is sluggish. The product of general Formula I is obtained either by filtration or by evaporating the solvent, dissolving the residue in chloroform, extracting with water, drying and then evaporating the chloroform solvent.

Sodium hydride can be used in place of the sodium alkoxide, and the solvent can be an ether such as THF or diethyl ether, etc.

b. Examples

The following example illustrates the synthesis of the compound of general Formula I by the general procedure described above.

EXAMPLE I

Synthesis of 5-(2-chloro-4-trifluoromethylphenoxy)-2-nitroacetophenone oxime-O-methyl ether a. Preparation of 3-(2-chloro-4-trifluoromethylphenoxy)acetophenone.

To a 250 ml. flask containing a solution of 13.92 grams of the potassium salt of 3-hydroxyacetophenone in 30 ml. of dry dimethylsulfoxide (DMSO), was added 17.12 grams (0.08 mole) of 3,4-dichlorobenzotrifluoride. The reaction solution was heated to 175° Centigrade for six hours, and then cooled and stirred at ambient temperature for 18 hours. The bulk of the DMSO was removed by evaporation, and the remaining dark residue was stirred with diethyl ether for 15 minutes and filtered. The filtrate was extracted once with water, once with sodium hydroxide, once with a saturated sodium chloride solution, dried over anhydrous MgSO$_4$, filtered, decolorized with charcoal, and evaporated to dryness leaving 16.04 grams of a dark red oil of 3-(2-chloro-4-trifluoromethylphenoxy)acetophenone. The material was further purified by passing through a neutral, grade III alumina column.

b. Nitration of 3-(2-chloro-4-trifluoromethylphenoxy) acetophenone

To a 100 milliliter (ml.) flask containing a solution of 26 ml. of concentrated sulfuric acid (H$_2$SO$_4$), and 16 ml. of ethylenedichloride (EDC), which was cooled to zero (0°) degrees Centigrade, 6.28 grams, (0.02 mole) of the dark red oil of 3-(2-chloro-4-trifluoromethylphenoxy)acetophenone (prepared as described herein) was added dropwise to form a brownish-black solution. When the addition of 3-(2-chloro-4-trifluoromethylphenoxy)acetophenone was completed, dry potassium nitrate (KNO$_3$), (2.0 grams, 0.020 mole) was added in small portions over a 20 minute period so as to maintain the reaction mixture below 4° Centigrade. The reaction mixture was stirred for 0.5 hours at 0° Centigrade. It was then poured into 250 ml. of ice and water, and the resulting mixture was mixed with 200 ml. of chloroform, (CHCl$_3$). The organic layer was separated, and then extracted twice with water, once with a saturated sodium chloride solution, and then dried over anhydrous magnesium sulfate, and then filtered. The organic solvent was evaporated off to yield 6.51 grams of an orange oil which analysis showed was a mixture of two positional isomers, one of which was 5-(2-chloro-4-trifluoromethylphenoxy)-2-nitroacetophenone. The mixture was separated into two fractions by high pressure liquid chromatography (HPLC) using diethyl ether as the eluant.

The diethylether was stripped from fraction #1, leaving 2.37 grams of an orange oil of 5-(2-chloro-4-trifluoromethylphenoxy)-2-nitroacetophenone.

Nuclear magnetic resonance [(NMR) (CDCl$_3$)]: 2.47δ(sing., 3H), 6.78–8.21δ (mult. 6H); Infra Red (IR): 1710, 1575, 1520, 1400, 1315 cm$^{-1}$; Mass Spectra (MS) molecular ion at m/e 359.

c. Synthesis of 5-(2-chloro-4-trifluoromethylphenoxy)-2-nitroacetophenoneoxime A 100 ml. flask was charged with a solution of 2.0 grams (0.0056 mole) of the orange oil, 5-(2-chloro-4-trifluoromethylphenoxy)-2-nitroacetophenone, in 10 ml. of absolute ethanol and 10 ml. of dry benzene. A solution of hydroxylamine hydrochloride (0.77 grams, 0.011 mole) in 15 ml. of absolute ethanol was added followed by addition of 1.12 grams (0.011 mole) of an acid acceptor triethylamine. The reaction mixture was then refluxed; when 20 ml. of solvent was distilled off, an additional 15 ml. of benzene was added. Refluxing was continued until 15 ml. of solvent distilled off, and then the remaining solution was refluxed for 16 hours, with the formation of a mixture of the syn and anti isomers of 5-(2-chloro-4-trifluoromethylphenoxy)-2-nitroacetophenone oxime. The solvent was stripped from the mixture, and the residue was dissolved in chloroform. The chloroform solution was extracted twice with water, then with a saturated solution of sodium chloride, and then dried over anhydrous magnesium sulfate.

The chloroform solution was filtered and the solvent (chloroform) was evaporated to yield 2.03 grams of an orange oil of 5-(2-chloro-4-trifluoromethylphenoxy)-2-nitroacetophenone oxime (anti and syn), which had the following:

Mass spectra (MS): molecular ion at m/e 374

Syn and Anti NMR (CDCl$_3$): 2:138δ (sing., 3H), 6.91–8.178δ (mult., 6-H), 9.338δ (sing., 1H)

Syn and Anti IR: 3100 broad, 1605, 1575, 1520, 1400 cm$^{-1}$ d. Formation of the anti and syn Isomers of 5-(2-chloro-4-trifluoromethylphenoxy)-2-nitro acetophenone oxime-O-methyl ether A solution of 0.10 grams (0.0045 ml.) of sodium metal in 5 ml. of methanol under nitrogen was charged into a 25 ml. flask. When all of the sodium had reacted, 1.50 grams (0.004 mole) of the 5-(2-chloro-4-trifluoromethylphenoxy)-2-nitroacetophenone oxime (anti and syn) prepared as described, and dissolved in 3 ml. of methanol was added, and the solution stirred. Methyliodide (0.64 grams, 0.0045 mole) was added next to the solution; and the resulting mixture was stirred at ambient temperature under nitrogen for forty-two (42) hours. The solvent was stripped from the solution and the residue was dissolved in methylene chloride (CH$_2$Cl$_2$). The CH$_2$Cl$_2$ solution was extracted twice with water and once with a saturated sodium chloride solution, and then dried over anhydrous magnesium sulfate. The CH$_2$Cl$_2$ solution was then filtered and the solvent removed by evaporation to yield 1.84 grams of an orange oil containing the anti and syn isomers of 5-(2-chloro-4-trifluoromethylphenoxy)-2-nitro acetophenone oxime-O-methyl ether. The orange oil was purified by chromatography by dissolving it into 5 ml. of ethyl ether and placing it on top of an eight inch by 21 mm. column of grade III alumina. The column was eluted with diethyl ether and the desired fractions were collected. The solvent was removed to yield 0.49 grams of a yellow oil of anti and syn isomers of 5-(2-chloro-4-trifluoromethylphenoxy)-2-nitro-O-acetophenone oxime.

MS: Molecular ion at m/e. 388

Syn and Anti IR: 2965, 1605, 1570, 1520, 1400 cm$^{-1}$

Syn and Anti NMR (CDCl$_3$): 2.31$\delta$ and 2.25$\delta$ (sing., 3H), 3.69$\delta$ and 3.91 (sing., 3H), 6.85–8.19$\delta$ (mult.6H)

Applications of the Compositions Against Weeds

The novel compounds of this invention are particularly valuable for preemergence and postemergence weed control because they are toxic to many species and groups of weeds and are relatively nontoxic to many beneficial plants. The exact amount of one or more of the compounds described herein required depends upon a variety of factors, including the hardiness of the particular weed species, the weather, the type of soil, the method of application, the kind of beneficial plants in the same area, and the like. Thus, while the application of up to only about 0.1 pounds of active compound per acre may be sufficient for good control of a light infestation of weeds growing under adverse conditions, the application of 2 pounds or more of an active compound per acre may be required for good control of a dense infestation of hardy perennial weeds growing under favorable conditions. The preferred compounds mentioned herein are generally used at the lower application rates such as from 0.1 to 10 pounds per acre; the less preferred but generally useful compounds are generally applied at the higher applications of from 10 to 20 pounds per acre, and those compounds which are intermediate between the most preferred compounds and the generally useful compounds are generally applied at rates from 5 to 15 pounds per acre.

a. Examples of Weeds Which May Be Controlled By The Compounds Described Herein

Weeds are undesirable plants growing where they are not wanted and may be classified as broadleaf or grassy weeds, a classification which includes many types of known weeds. It is believed that many weeds may be controlled by the compositions set forth herein, when applied in a herbicidally effective amount. These include field pennycress, ryegrass, goosegrass, chickweed, purslane, smartweed, knotweed, wild buckwheat, kochia, medic, corn cockle, ragweed, sow-thistle, croton, cuphea, dodder, fumitory, groundsel, hempnettle, knawel, spurge, spurry, emex, jungle rice, pondweed, dogfennel, carpetweed, bedstraw, ducksalad, naiad, cheatgrass, fall panicum, witchgrass, switchgrass, watergrass, teaweed, wild turnip, and sprangletop; biennials such as wild carrot, matricaria, wild barley, campion, chamomile, burdock, mullein, roundleaved mallow, bull thistle, houndstongue, moth mullein, and purple star thistle; or perennials such as white cockle, perennial ryegrass, quackgrass, Canada thistle, hedge bindweed, Bermuda grass, sheep sorrel, curly dock, nutgrass, field chickweed, dandelion, campanula, field bindweed, Russian knapweed mesquite, toadflax, yarrow, aster, gromwell, horsetail, ironweed, sesbania, bulrush, cat-tail, wintercress, horsenettle, nutsedge, milkweed, and sicklepod.

The genus of weeds the compounds, particularly the most preferred compounds, appear most active against preemergence are: *Sorghum, Sesbania, Fatua* and *Echinochola.*

Weed species against which the compounds of the invention appear to be most effective (preemergence) are: *Sorghum halepense* (johnsongrass), Sesbania spp. (coffeeweed), *Avena fatua* (L) (wild oats), and *Echinochola crusgalli* (L) (barnyard grass).

The genus of weeds that the compounds, particularly the most preferred compounds, appear most active against postemergence are: *Sida, Datura, Brassica, Setaria, Gossypium, Sorghum, Sesbania, Abutilon, Ipomoea, Avena,* and *Echinochola.*

The compositions, particularly, the most preferred compositions, appear to be most effective when applied postemergence against the weed species *Sida spinosa* (L) (teaweed, prickly sida), *Datura stramonium* (L) (jimsonweed), *Brassica kaber* (DC) (wild mustard), *Setaria glauca* (L) (yellow foxtail), *Gossypium hirsutum* (L) (cotton), Sesbania spp. (coffeeweed), *Abutilon theophrasti* (L) (velvetleaf), *Ipomoea purpurea* (L) Roth (tall morningglory), *Sorghum halepense* (johnsongrass), *Avena fatua* (L) (wild oats) and *Echinochola crusgalli* (L) (barnyard grass).

b. Description of the Method of Controlling Weeds

As used herein and in the claims, the method of controlling the weeds comprises contacting the weeds with a herbicidally effective amount of a composition represented by the general formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, but preferably after they emerge, with one or more of the compounds represented by Formula I described herein. The phrase "the herbicidally effective amount" refers to that amount required under the environmental conditions in order to effectively control, that is, by which the weeds are killed or are injured so severely as not to be able to recover from the application of the compound.

c. General Application of the Compounds

For practical use as herbicides, the compounds of this invention are generally incorporated into herbicidal formulations which comprise an inert carrier and a herbicidally toxic amount of a compound mentioned herein. Such herbicidal formulations enable the active compound to be applied conveniently to the side of the weed infestation in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust compositions.

In some cases, the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal formulation according to this invention is illustrated by the following example, in which the quantities are in parts by weight.

EXAMPLE III
Preparation of a Dust

| Product of Example I | 10 |
|---|---|
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Use of Compounds Alone Or In Mixtures

Although all of the compounds described herein and represented by the general formula described herein are useful as herbicides, some of these are preferred and are better for applications against weeds. In general, all of the compounds described herein may be used either alone or together in mixtures of the compounds described herein. When used in mixtures the amount or ratio of one compound to another may vary from 0.01 to 100. The amount to use ranges from 0.10 pounds per acre to 20 pounds per acre depending upon the conditions.

e. Manner of Application Of The Compounds Of This Invention In Formulations

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulation and the purpose for which it is designed, but generally the herbicidal formulations will comprise from about 0.05 to about 95 percent by weight of the active compounds of this invention. In a preferred embodiment of this invention, the herbidical formulations will comprise from about 5 to 75 percent by weight of the active compound. The formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples of Other Pesticides And Herbicides For Combinations

The other herbicides, defoliants, desiccants, and plant growth inhibitors, with which the compounds of this invention can be used in the herbicidal formulations to control weeds, can include: chlorophenoxy herbicides; such as 2,4-D, 2,4,5-T, MCPA, MCPB, 4-2,4-DB, 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, perbulate, vernolate and the like; substituted urea herbicides such as norea, siduron, dichloroal urea, chloroxuron, cycluron, fenuron, monuron, monuron TCA, diuron, linuron, monolinuron, neburon, buturon, trimeturon, and the like; symmetrical triazine herbicides such as simazine, chlorazine, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloropropionic acid, 2,2,3-TPA, and the like; chlorinated benzoic acid and phenylacetic acid herbicides such as 2,3,6-TBA, 2,3,5,6-TBA, dicamba, tricamba, amiben, fenac, PBA, 2-methoxy-3,5-dichlorophenylacetic acid, 3-methoxy-2, 6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazide, phenyl mercuric acetate, endothall, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, dipheratril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil, and the like. Such herbicides can also be used with the compositions of this invention in the form of their salts, esters, amides, and other derivatives whenever applicable to the particular parent compounds.

g. Examples of Herbicidal Control

The following examples illustrate the utility of the compositions described herein for the control of weeds.

These tests described herein were conducted in a laboratory under laboratory conditions in accordance with standard herbicidal testing procedures for pre-emergence and postemergence control. The plants are observed for 21 days after treatment, and the observations were recorded.

EXAMPLE II

When 5-(2-chloro-4-trifluoromethylphenoxy)-2-nitroacetophenone oxime-O-methyl ether (from Example I) was applied preemergence at ten (10) pounds per acre to *Sorghum halepense* (L) (johnsongrass-from seed); *Sesbania* spp. (coffeeweed), *Avena fatua* (L) (wild oats), and *Echinochola crusgalli* (L) (barnyard grass), the weeds were killed by 21 days.

EXAMPLE III

When 5-(2-chloro-4-trifluoromethylphenoxy)-2-nitroacetophenone oxime-O-methyl ether (from Example I) was applied postemergence at ten (10) pounds per acre to; *Sida spinosa* (L) (teaweed, also called prickly sida); *Datura stramonium* (jimsonweed), *Brassica kaber* (wild mustard), *Setaria glauca* (L) (yellow foxtail), *Gossypium hirsutum* (cotton), *Sesbania* spp. (coffeeweed), *Abutilon theophrasti* (velvetleaf), *Ipomoea purpurea* (L) Roth (tall morningglory), *Sorghum halepense* (johnsongrass), *Avena fatua* (L) (wild oats), and *Echinochola crusgalli* (L) (barnyard grass), all the weeds were killed by 21 days.

While the invention has been described with reference to specific details of certain illustrative embodiments, it is not intended that it shall be limited thereby except insofar as such details appear in the accompanying claims.

I claim:

1. In a method of controlling weed growth wherein a herbicidal amount of a herbicide is applied to the weeds subsequent to their emergence from the growth medium wherein the improvement resides in using as the herbicide a compound represented by the formula:

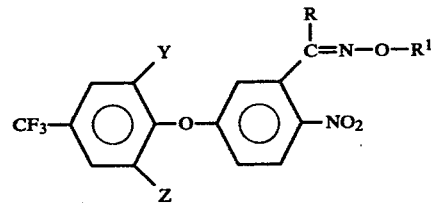

wherein:
Y and Z are independently hydrogen or chlorine;
R is hydrogen or alkyl of up to 3 carbon atoms; and
$R^1$ is alkyl of up to 4 carbon atoms.

2. The improvement of claim 1 wherein Y is chlorine and Z is hydrogen.
3. The improvement of claim 1 wherein R is methyl.
4. The improvement of claim 1 wherein $R^1$ is methyl.
5. The improvement of claim 1 wherein the herbicide is the compound 5-(2-chloro-4-trifluoromethylphenoxy)-2-nitroacetophnone oxime-O-methyl ether.

* * * * *